(12) United States Patent
Jeong et al.

(10) Patent No.: US 7,836,766 B2
(45) Date of Patent: Nov. 23, 2010

(54) METHOD OF ACQUIRING AN ULTRASOUND IMAGE

(75) Inventors: Mok Keun Jeong, Seoul (KR); Sung Jae Kwon, Seoul (KR); Ra Young Yoon, Seoul (KR)

(73) Assignee: Medison Co., Ltd., Kangwon-do (KR)

( * ) Notice: Subject to any disclaimer, the term of this patent is extended or adjusted under 35 U.S.C. 154(b) by 387 days.

(21) Appl. No.: 12/159,390

(22) PCT Filed: Dec. 27, 2006

(86) PCT No.: PCT/KR2006/005757

§ 371 (c)(1),
(2), (4) Date: Jun. 26, 2008

(87) PCT Pub. No.: WO2007/075040

PCT Pub. Date: Jul. 5, 2007

(65) Prior Publication Data

US 2009/0003128 A1    Jan. 1, 2009

(30) Foreign Application Priority Data

Dec. 28, 2005  (KR) .................... 10-2005-0131562

(51) Int. Cl.
*G01N 29/04* (2006.01)
*A61B 8/00* (2006.01)

(52) U.S. Cl. .............................. 73/603; 73/606; 73/632; 600/447; 600/459

(58) Field of Classification Search ................. 73/603, 73/604, 606, 609, 632; 600/447, 459
See application file for complete search history.

(56) References Cited

U.S. PATENT DOCUMENTS

| | | | | |
|---|---|---|---|---|
| 4,693,120 A | * | 9/1987 | Robinson | 73/618 |
| 4,972,838 A | | 11/1990 | Yamazaki | |
| 5,129,399 A | | 7/1992 | Hirama | |
| 5,181,778 A | * | 1/1993 | Beller | 374/119 |
| 6,971,992 B2 | | 12/2005 | Cerofolini | |
| 6,974,417 B2 | * | 12/2005 | Lockwood et al. | 600/459 |
| 7,029,445 B2 | * | 4/2006 | Shinomura et al. | 600/443 |
| 2009/0099455 A1 | * | 4/2009 | Katsuyama | 600/459 |
| 2010/0076312 A1 | * | 3/2010 | Katsuyama | 600/443 |

OTHER PUBLICATIONS

International Search Report for PCT/KR2006/005757, Mailed Apr. 6, 2007 (3 pages).
Written Opinion of the International Searching Authority for PCT/US2006/005757, Mailed Apr. 6, 2007 (4 pages).

* cited by examiner

*Primary Examiner*—J M Saint Surin
(74) *Attorney, Agent, or Firm*—Jones Day

(57) ABSTRACT

The present invention relates to a method of acquiring an ultrasound image in an ultrasound imaging system having an array transducer, comprising: a) setting an image point at a predetermined depth on an ultrasound image acquired based on a reference speed of sound for a target object; b) setting a range of speed of sound with reference to the reference speed; c) setting a plurality of speeds of sound in a predetermined interval within the range of speed of sound; d) acquiring ultrasound images at each speed of sound; e) calculating an amplitude of an image point set at a predetermined depth of each ultrasound image; f) determining a real speed of sound in the target object based on the calculated amplitude; and g) acquiring an ultrasound image based on the determined real speed of sound in the target object.

8 Claims, 5 Drawing Sheets

[Fig. 1]
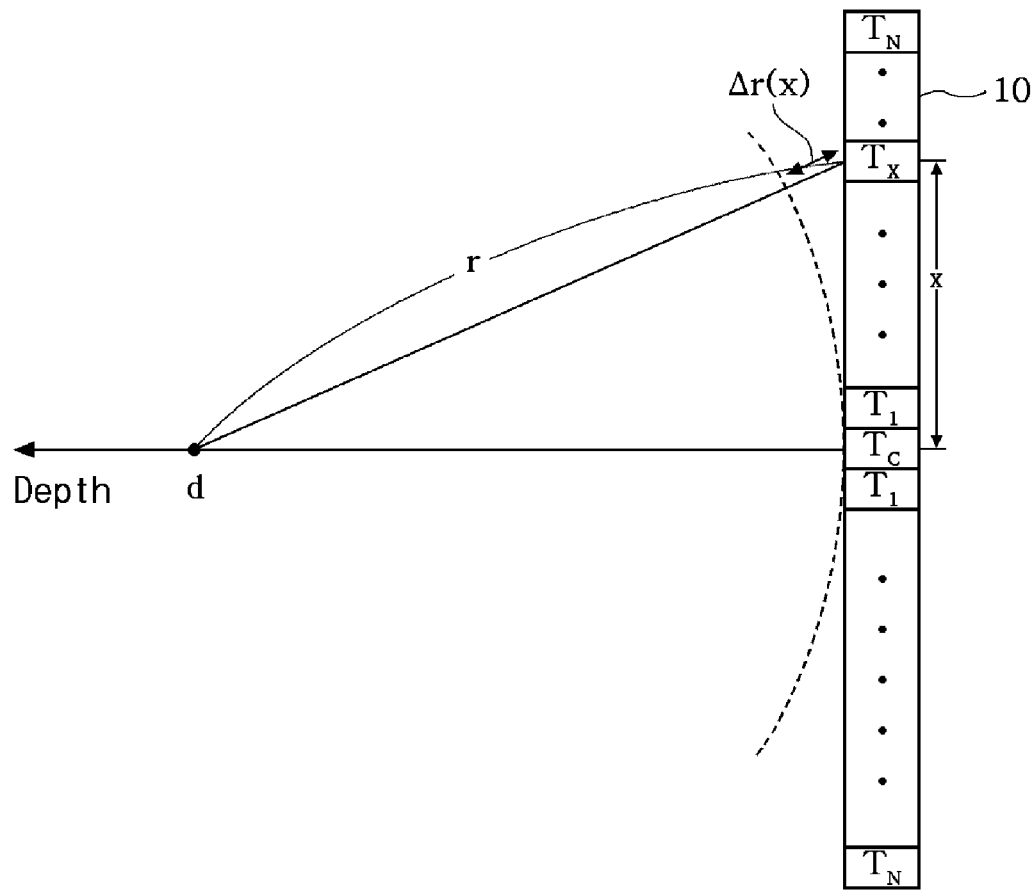
[Fig. 2]
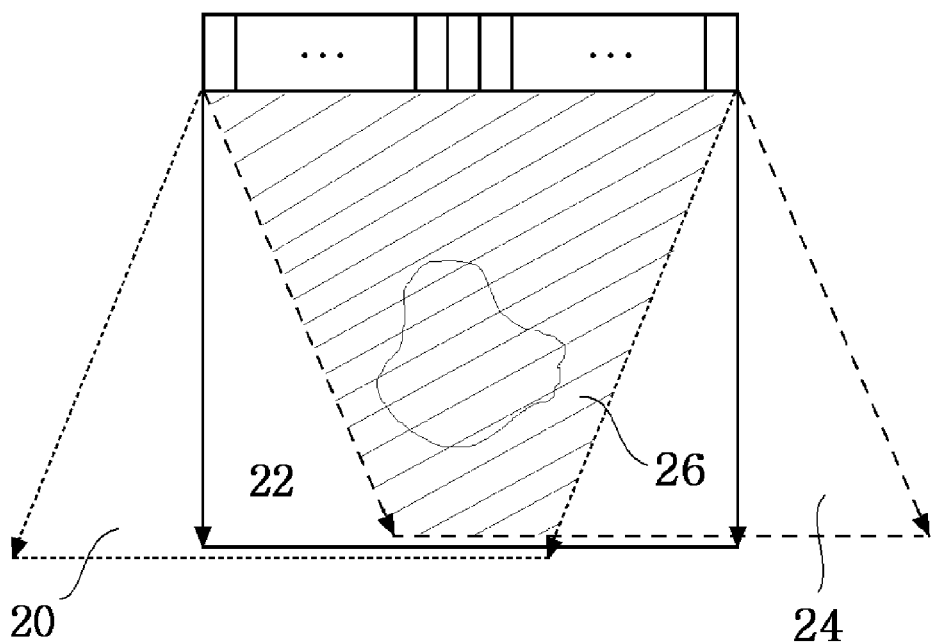

[Fig. 3]
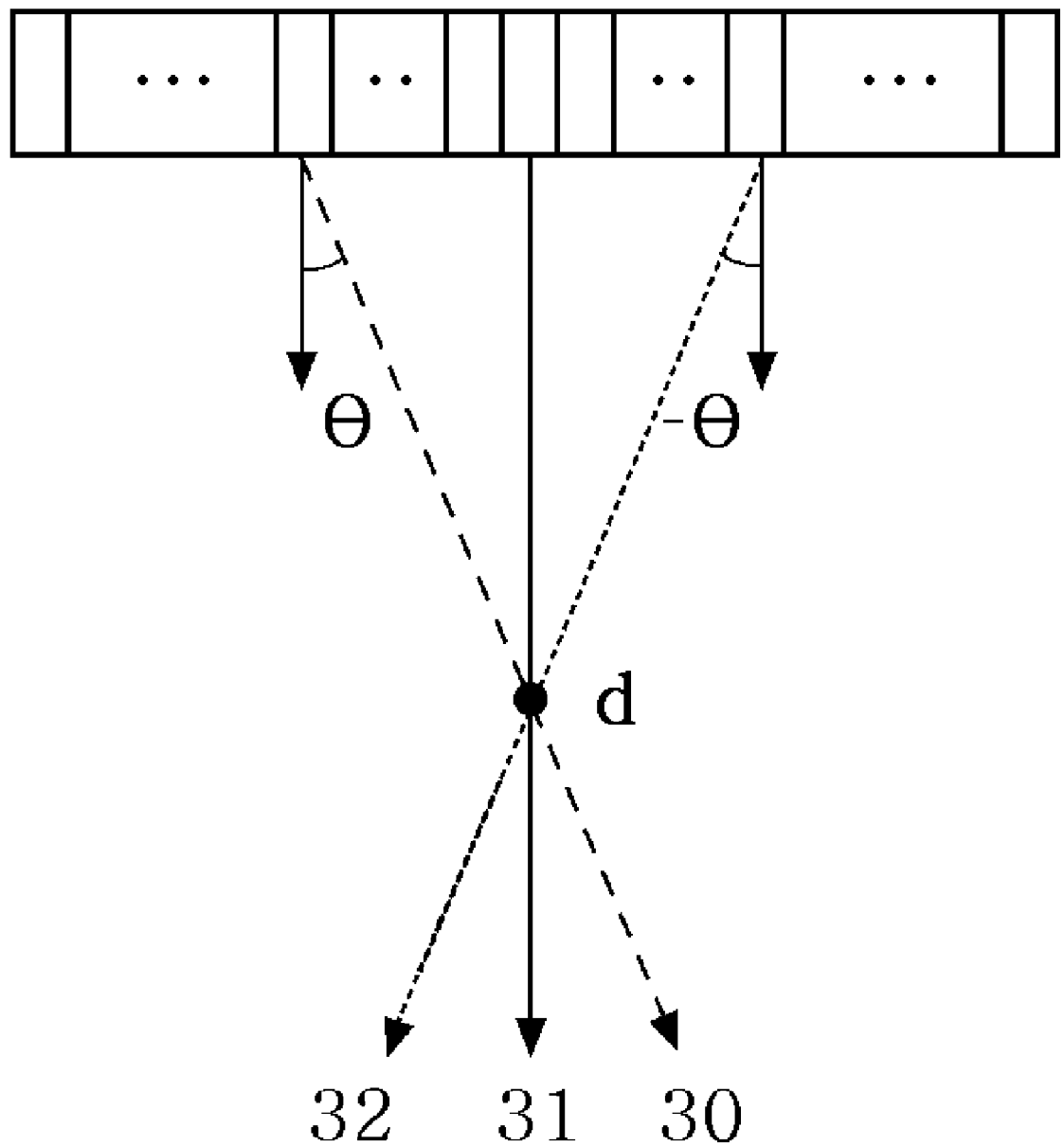

[Fig. 4]
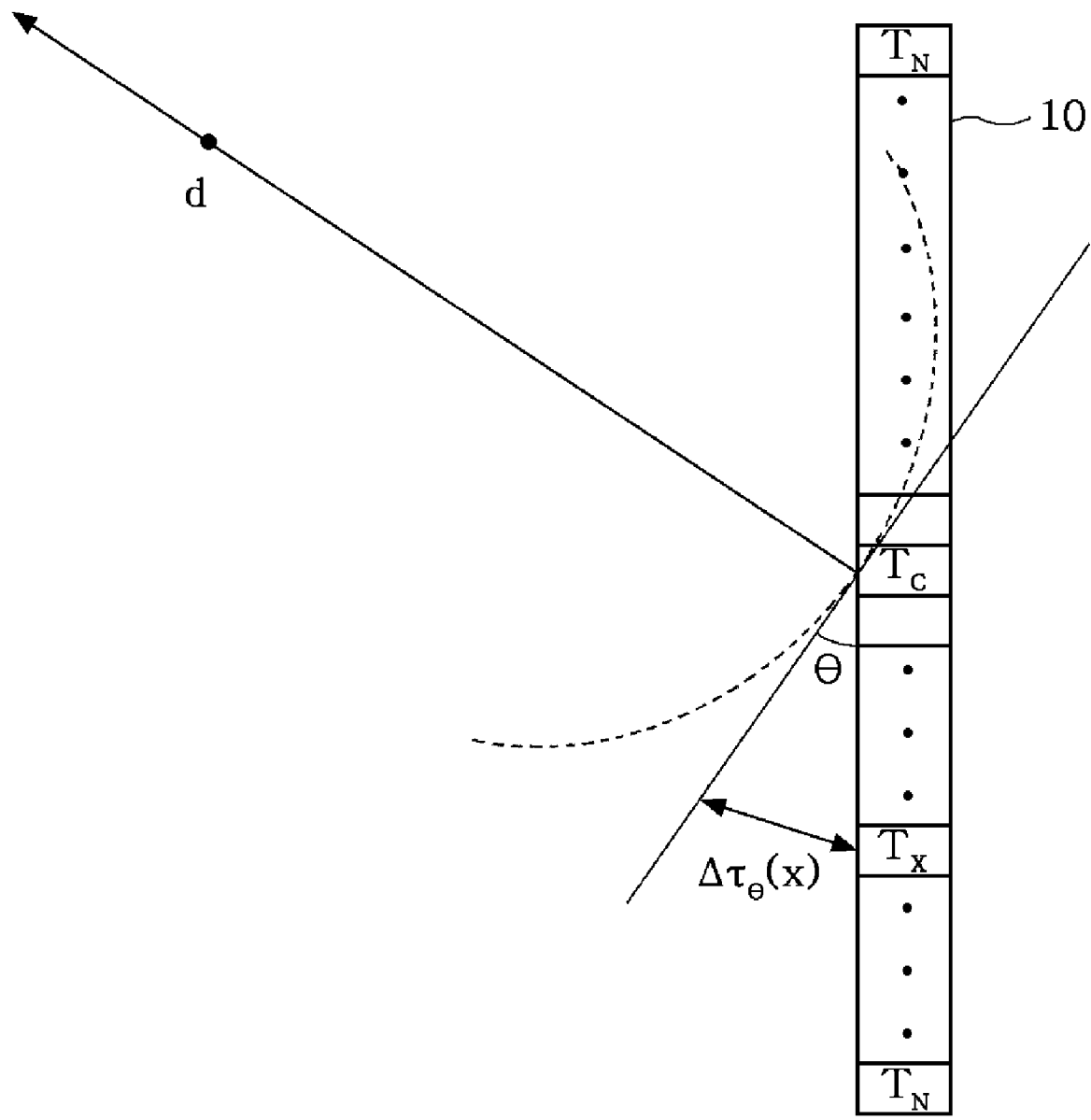

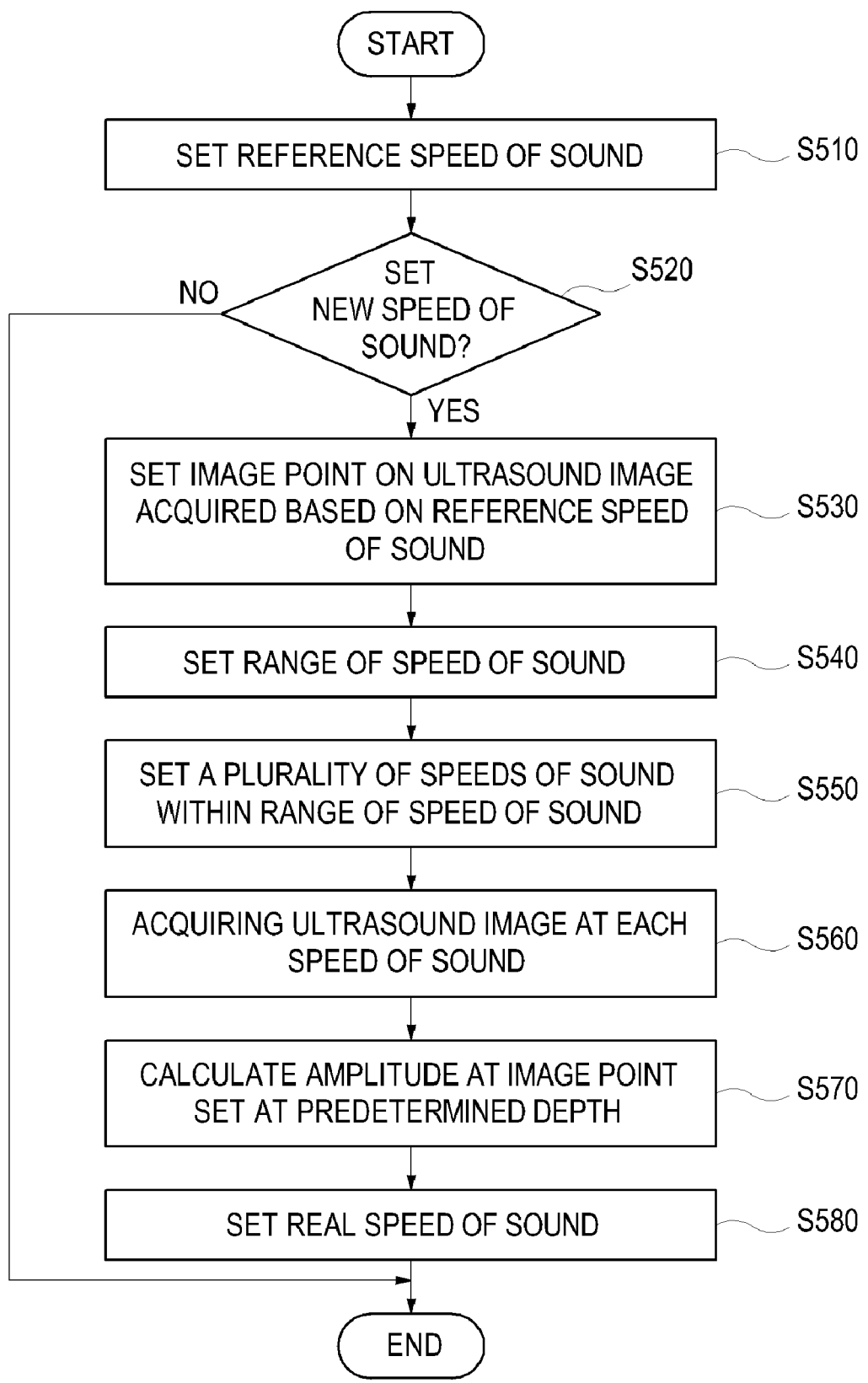
[Fig. 5]

[Fig. 6]
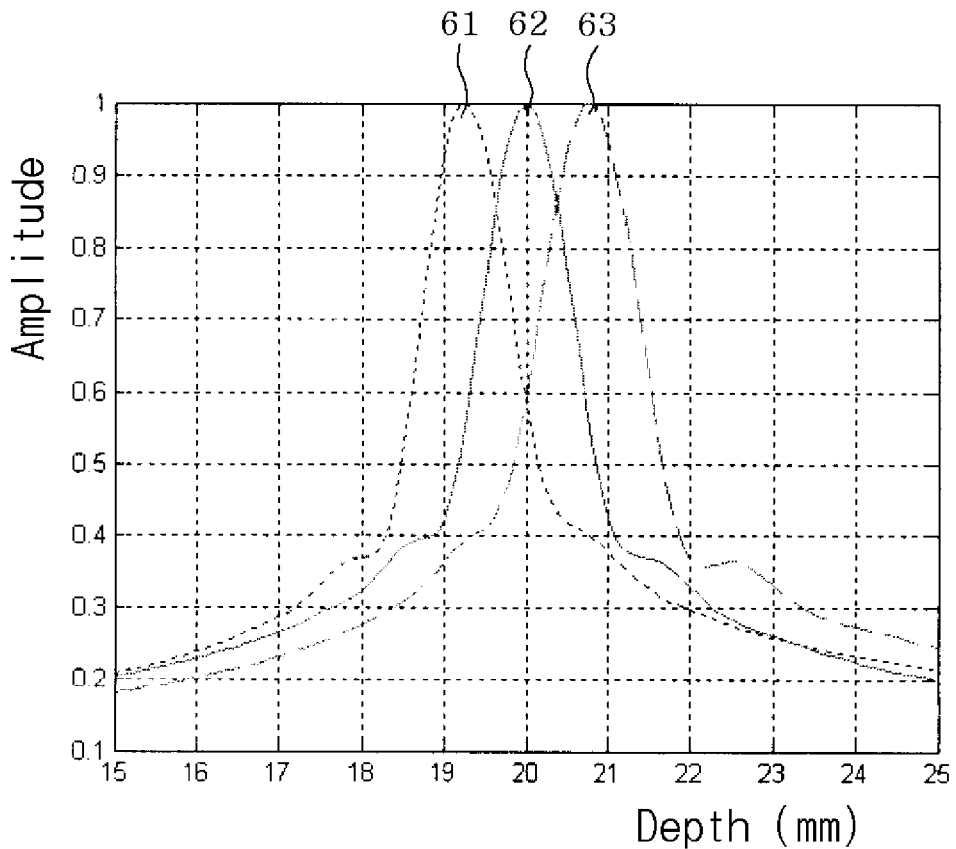
[Fig. 7]
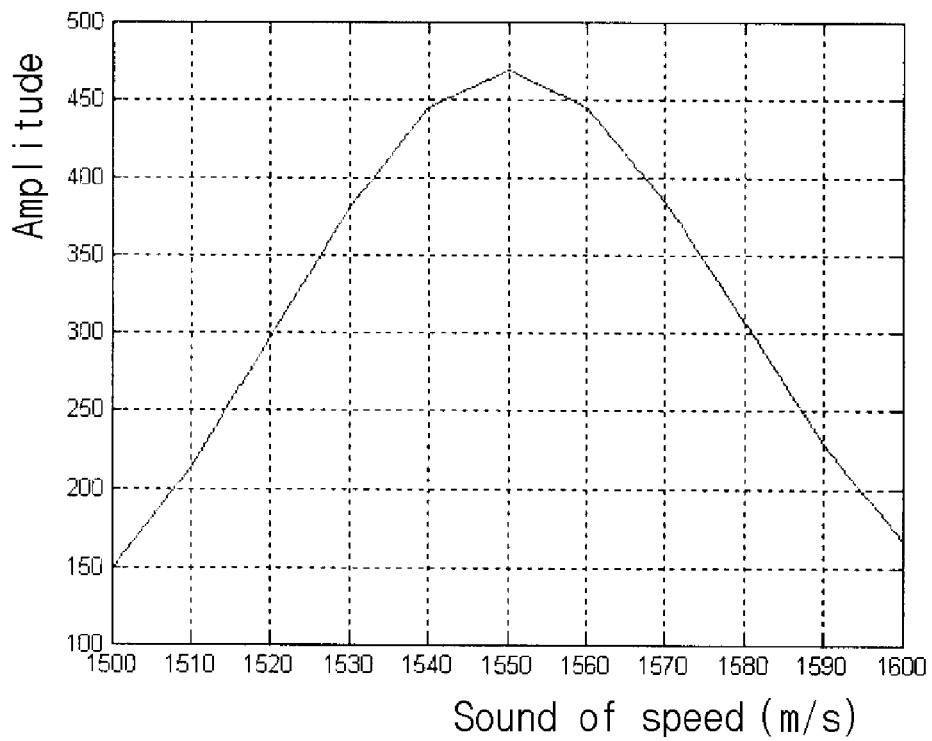

METHOD OF ACQUIRING AN ULTRASOUND IMAGE

TECHNICAL FIELD

The present invention generally relates to image forming methods, and more particularly to a method of forming an ultrasound compound image while correcting a focusing error.

BACKGROUND ART

An ultrasound imaging system transmits ultrasound signals into a target object and receives ultrasound echo signals. The echo signals are converted into electrical signals in a probe. The ultrasound imaging system performs signal processing for the electrical signals, thereby forming an ultrasound image. The ultrasound imaging system has been extensively used in the medical procession due to its non-invasive and non-destructive nature. In order to acquire a high-resolution ultrasound image, various techniques have been studied and researched in the ultrasound imaging system. Recently, an array transducer comprising a plurality of transducer elements is used to acquire the high-resolution ultrasound image. Also, the transmit focusing and receive focusing methods have been adopted for acquiring high-resolution ultrasound images.

FIG. 1 is a schematic diagram illustrating the delays of ultrasound echo signals arriving at each transducer element in an array transducer. A predetermined delay profile of transmit pulse signals is established so that ultrasound signals produced at the array transducer 10 are focused on a focal point, wherein each transducer element then produces ultrasound signals according to such predetermined delay profile. Ultrasound echo signals reflected from the focal point arrive at each transducer element in different times.

As shown in FIG. 1, an ultrasound echo signal reflected from the focal point travels a distance of "d" to arrive at a transducer element Tc, while an ultrasound echo signal reflected from the focal point travels a distance of r (r=d+Δr(x)) to reach a transducer element Tx. That is, the ultrasound echo signal received at the transducer element Tx is delayed by Δr(x) compared to the ultrasound echo signal received at the transducer element Tc. The ultrasound echo signals received at each transducer element are converted into electrical signals (hereinafter referred to as receive signals). The receive signals should be focused in order to obtain image signals. In focusing the receive signals, the delays of the ultrasound echo signals arriving at each transducer element should be compensated. A receive focusing delay technique is usually adopted to compensate for the delays of the ultrasound echo signals.

The delay of the ultrasound echo signal arriving at each transducer element can be calculated using the following equation:

$$\Delta \tau(x) = \frac{\Delta r(x)}{v} = \frac{\sqrt{x^2 + d^2} - d}{v} \quad (1)$$

wherein, $\Delta \tau(x)$ represents a time delay of an ultrasound echo signal arriving at the transducer element Tx, v represents a propagation speed of the ultrasound signal (speed of sound) in a target object, x represents a distance between the elements Tc and Tx and d represents a distance between the focal point and the transducer element Tc. d may be calculated using the following equation:

$$d = vt \quad (2)$$

Wherein, t represents a time for the ultrasound signal to arrive at the transducer element Tc from the focal point.

As shown in the above equations, the speed of sound in the target object is important for determining the delays of ultrasound echo signals. When the target object is a human body, the speed of sound is generally set to 1540 m/s, which is an average speed in the soft tissues of the human body. However, the speed of sound is 1460 m/s in fat, 1555 m/s in liver, 1560 m/s in blood and 1600 m/s in muscle. That is, the speed of sound is changed according to the type of media. Therefore, if the fixed speed of sound is used, then a calculation error in the delays of ultrasound echo signals arriving at each transducer element may occur.

Recently, a compound ultrasound image is used to enhance the quality of an ultrasound image. In order to obtain the compound ultrasound image, the scan lines are steered in different angles and then ultrasound images are obtained at each angle of the scan lines. Thereafter, the obtained ultrasound images are spatially compounded, thereby forming the compound ultrasound image. In this case, if the speed of sound is not accurately set, then the delays of ultrasound echo signals arriving at each transducer element for each steered scan line cannot be accurately calculated. Thus, the pixels corresponding to an identical image of the target object may not be exactly overlapped. Therefore, the overall compound image becomes dark and a signal to noise ratio (SNR) and a contrast may be decreased.

DISCLOSURE OF INVENTION

Technical Problem

As described above, if the speed of sound is incorrectly set for the target object, then image pixels corresponding to an identical position of the target object in the ultrasound images obtained by steering a scan angle cannot be overlapped in compounding the ultrasound images. Therefore, the compound image becomes dark and SNR and contrast are decreased.

Technical Solution

The present invention provides a method of acquiring a compound ultrasound image having a high resolution by determining the real speed of sound in a target object.

In accordance with an aspect of the present invention, there is provided a method of acquiring an ultrasound image in an ultrasound imaging system having an array transducer, comprising: a) setting an image point at a predetermined depth on an ultrasound image acquired based on a reference speed of sound for a target object; b) setting a range of speed of sound with reference to the reference speed; c) setting a plurality of speeds of sound in a predetermined interval within the range of speed of sound; d) acquiring ultrasound images at each speed of sound; e) calculating an amplitude of an image point set at a predetermined depth of each ultrasound image; f) determining a real speed of sound in the target object based on the calculated amplitude; and g) acquiring an ultrasound image based on the determined real speed of sound in the target object.

In accordance with another embodiment of the present invention, there is provided a method of acquiring an ultrasound image in an ultrasound imaging system having an array transducer, comprising: a) setting an image point at a predetermined depth on an ultrasound image acquired based on a reference speed of sound for a target object; b) setting a range of speed of sound with reference to the reference speed; c) setting a plurality of speeds of sound in a predetermined interval within the range of speed of sound; d) acquiring ultrasound images at each speed of sound; e) calculating an amplitude of an image point set at a predetermined depth of each ultrasound image; f) determining a real speed of sound in the target object based on the calculated amplitude; g) acquiring a plurality of ultrasound images by steering scan lines in predetermined angles based on the determined real speed of sound; and h) forming a compound ultrasound image by compounding the acquired ultrasound images.

BRIEF DESCRIPTION OF THE DRAWINGS

FIG. 1 is a schematic diagram illustrating delays of ultrasound echo signals arriving at each transducer element in an array transducer.

FIG. 2 is a schematic diagram showing an example of acquiring a compound image from a plurality of ultrasound image obtained by steered scan lines.

FIG. 3 is a schematic diagram showing an example of illustrating acquisition of ultrasound image data from a focal point at which steered scan lines are overlapped.

FIG. 4 is a diagram showing an example of a delay of an ultrasound echo signal according to a steered scan line.

FIG. 5 is a flowchart illustrating a method of determining a real speed of sound in a target object in accordance with an embodiment of the present invention.

FIG. 6 is a graph illustrating a change in amplitude of image signals with respect to depth at differently set speeds of sound.

FIG. 7 is a graph illustrating a change of amplitude of image signals corresponding to the image point according to a change of the speed of sound.

BEST MODE FOR CARRYING OUT THE INVENTION

FIG. 2 is a schematic diagram illustrating an example of acquiring a compound image from a plurality of ultrasound images obtained by steered scan lines.

As shown in FIG. 2, a first ultrasound image 20, a second ultrasound image 22, a third ultrasound image 24, which are acquired by scan lines steered in first, second and third angles, respectively, are overlapped, thereby forming a compound ultrasound image 26. In FIG. 2, a dashed region 26 represents the compound ultrasound image formed by combining the first, second and third ultrasound images 20, 22 and 24.

FIG. 3 is a schematic diagram showing an example of illustrating the acquisition of ultrasound image data from a focal point at which steered scan lines are overlapped. As shown therein, the compound image is formed by using image data obtained from a focal point, at which scan lines steered in predetermined angles of θ and –θ and a scan line perpendicular to a scan head, are overlapped.

FIG. 4 is a diagram illustrating an example of a delay of an ultrasound echo signal according to a steered scan line. Since the scan line set from a transducer element Tc is steered in an angle of θ as shown in FIG. 4, the steering delay of an ultrasound echo signal reflected from a focal point placed on the scan line may occur. The steering delay $\Delta\tau_\theta(x)$ at a transducer element Tx away from the transducer element Tc by x may be approximately calculated by the following equation.

$$\Delta\tau_\theta(x) \approx \frac{x \cdot \sin\theta}{v} \quad (3)$$

wherein, θ represents the steering angle and v represent the speed of sound. As can be seen through the equation (3), in order to calculate the steering delay at each transducer, the speed of sound should be accurately set in the target object. If the steering delay $\Delta\tau_\theta(x)$ is not accurately calculated, then the image signals acquired from identical focal points on the steered scan lines may not be overlapped.

FIG. 5 is a flowchart illustrating a method of determining a real speed of sound in a target object in accordance with an embodiment of the present invention. For the sake of convenience, the method of calculating the real speed of sound in the target object will be described by using an ultrasound image acquired through scan lines 31 perpendicular to the scan head of the array transducer 10. Also, an array transducer of a linear structure is used and the ultrasound signals are transmitted by using a plurality of channels.

As shown in FIG. 5, a predetermined speed of sound (hereinafter referred to as a reference speed) is set at step S510. The reference speed may be arbitrarily set according to the type of target objects. It is preferable to set a mean speed at media constructing the target object as a reference speed. Also, various reference speeds may be previously set to the target objects, which are frequently examined by using the ultrasound imaging system, such as a human body. The previously set reference speeds may be stored and then an appropriate reference speed may be used according to the type of the target object. For example, if the target object is a human body, then the reference speed may be a mean speed in fat, blood, muscle and the like. Typically, the mean speed of the human body may be set to a speed in a soft tissue of 1540 m/s.

Subsequently, it is checked whether a new speed of sound is set at step S520. If it is determined not to set the new speed of sound, then an ultrasound image is acquired by using the reference speed of sound set at step S510. On the other hand, if it is determined to set the new speed of sound, then an image point is selected in a predetermined depth on an ultrasound image acquired by using the reference speed of sound at step S530. The image point may be arbitrarily selected on the ultrasound image by using one of various markers provided in the ultrasound imaging system. The setup of the new speed of sound may be carried out by using a setup button mounted on a predetermined position of the ultrasound imaging system. Also, a detecting sensor may be mounted on the probe of the ultrasound imaging system such that the new speed of sound is set when the probe is contacted to a surface of the target object.

In order to set the new speed of sound, a predetermined range of speed of sound is set with reference to the reference speed of sound at step S540. The range of speed of sound may be set to include the overall speeds of sound in media constructing the target object. Also, various ranges of speed of sound may be previously set to the target objects, which are frequently examined by using the ultrasound imaging system, such as a human body. The previously set ranges of the speed of sound may be stored. Then, an appropriate range of the speed of sound may be used according to the type of the target object such as the reference speed of sound.

After setting the range of the speed of sound, a plurality of speeds of sound are set in a predetermined interval from a slowest speed of sound within the range of variable speeds of sound at step S550. A plurality of ultrasound images are acquired at each of the set speeds of sound at step S560. Then, the brightness of the image point set in the predetermined depth of the target object is calculated at each acquired ultrasound image at step S570. The speed of sound applied to an ultrasound image having a maximum brightness is set as a real speed of sound of the target object at step S580.

FIG. 6 is a graph illustrating a change in amplitude of image signals with respect to depth at differently set speeds of sound. When a real speed of the sound in the target object is of 1550 m/s, curves 61, 62 and 63 are obtained by simulating that speeds of sound are set at 1500 m/s, 1550 m/s and 1600 m/s, respectively. The simulation is carried out by assuming that 92 transducers of 40 mm and a frequency of 7.5 MHz are used and the ultrasound signals are focused on the image point positioned at a depth of 20 mm.

As shown in FIG. 6, if the speed of sound is set faster than the real speed of sound, then maximum amplitude appears at a depth deeper than the depth of 20 mm by 0.8 mm. On the other hand, if the speed of sound is set slower than the real speed of sound, then maximum amplitude appears at a depth shallower than the depth of 20 mm by 0.7 mm. That is, in case of setting the image point at a depth of 20 mm, the amplitudes are about 0.6, 1 and 0.6 at the image point when the speed of sound is set to 1500 m/s, 1550 m/s and 1600 m/s, respectively. Therefore, the speed of sound of 1550 m/s is selected as a real speed of sound in the target object.

FIG. 7 is a graph showing a change in amplitude of image signals corresponding to the image point according to a change in the speed of sound. As shown in FIG. 7, the amplitude is calculated by changing the speed of sound from 1500 m/s to 1600 m/s in a predetermined interval, thereby obtaining a curve of the speed of sound to amplitude. The curve shown in FIG. 7 may be formed by curve-fitting the maximum points of each 2-order function obtained at each speed of sound. As shown therein, when the speed of sound is 1550 m/s, the amplitude becomes maximum. Therefore, the speed of sound of 1550 m/s may be adopted as a real speed of sound of the target object.

If the real speed of sound is set according to the above method, then the real speed of sound is applied to the equations (1) and (2), thereby accurately calculating the receive focusing delay and the steering delay. Since the delays are accurately calculated in accordance with one embodiment of the present invention, the steered scan lines can be accurately overlapped at the desirable image points. Therefore, a compound image having a high resolution can be acquired.

When the speed of sound is determined by using the amplitude of brightness at an image point, it may be difficult to determine the speed of sound due to noises. Therefore, a window of a predetermined size may be set on an image of the target object. Further, the sum of amplitudes of pixels included in the window may be used to determine the speed of sound of the target object in accordance with another embodiment of the present invention. This is so that a calculation error owing to the noises may be reduced.

While the present invention has been described and illustrated with respect to a preferred embodiment of the invention, it will be apparent to those skilled in the art that variations and modifications are possible without deviating from the broad principles and teachings of the present invention, which should be limited solely by the scope of the claims appended hereto.

INDUSTRIAL APPLICABILITY

As mentioned above, since the speed of sound in the target object is accurately determined, an enhanced compound image can be acquired.

The invention claimed is:

1. A method of acquiring an ultrasound image in an ultrasound imaging system having an array transducer, comprising:
   a) setting an image point at a predetermined depth on an ultrasound image acquired based on a reference speed of sound for a target object;
   b) setting a range of speed of sound with reference to the reference speed;
   c) setting a plurality of speeds of sound in a predetermined interval within the range of speed of sound;
   d) acquiring ultrasound images at each speed of sound;
   e) calculating an amplitude of an image point set at a predetermined depth of each ultrasound image;
   f) determining a real speed of sound in the target object based on the calculated amplitude; and
   g) acquiring an ultrasound image based on the determined real speed of sound in the target object.

2. The method of claim 1, wherein the step a) includes:
   a1) selecting the reference speed of sound previously set according to a type of the target object;
   a2) checking whether to set a new speed of sound for the target object;
   a3) if it is determined to set the new speed of sound at step a2), acquiring the ultrasound image based on the reference speed of sound; and
   a4) setting the image point on the acquired ultrasound image at the predetermined depth.

3. The method of claim 2, wherein the speed of sound applied to the ultrasound image having highest amplitude at the image point among the calculated amplitudes is determined as a real speed of sound of the target object.

4. The method of claim 3, wherein the reference speed of sound image is a mean speed of sound of media consisting of the target object.

5. A method of acquiring an ultrasound image in an ultrasound imaging system having an array transducer, comprising:
   a) setting an image point at a predetermined depth on an ultrasound image acquired based on a reference speed of sound for a target object;
   b) setting a range of speed of sound with reference to the reference speed;
   c) setting a plurality of speeds of sound in a predetermined interval within the range of speed of sound;
   d) acquiring ultrasound images at each speed of sound;
   e) calculating an amplitude of an image point set at a predetermined depth of each ultrasound image;
   f) determining a real speed of sound in the target object based on the calculated amplitude;
   g) acquiring a plurality of ultrasound images by steering scan lines in predetermined angles based on the determined real speed of sound; and
   h) forming a compound ultrasound image by compounding the acquired ultrasound images.

6. The method of claim 5, wherein the step a) includes:
   a1) selecting the reference speed of sound previously set according to a type of the target object;
   a2) checking whether to set a new speed of sound for the target object;

a3) if it is determined to set the new speed of sound at step a2), acquiring the ultrasound image based on the reference speed of sound; and
a4) setting the image point on the acquired ultrasound image at the predetermined depth.

7. The method of claim 6, wherein the speed of sound applied to the ultrasound image having highest amplitude at the image point among the calculated amplitudes is determined as a real speed of sound of the target object.

8. The method of claim 7, wherein the reference speed of sound image is a mean speed of sound of media consisting of the target object.

* * * * *